US009844597B2

(12) United States Patent
Chau et al.

(10) Patent No.: US 9,844,597 B2
(45) Date of Patent: Dec. 19, 2017

(54) BIOCOMPATIBLE IN SITU HYDROGEL

(71) Applicant: Hong Kong University of Science and Technology, Hong Kong (CN)

(72) Inventors: Ying Chau, Hong Kong (CN); Yu Yu, Hong Kong (CN); Jieying Zhong, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 14/782,999

(22) PCT Filed: Apr. 17, 2014

(86) PCT No.: PCT/CN2014/000420
§ 371 (c)(1),
(2) Date: Oct. 7, 2015

(87) PCT Pub. No.: WO2014/169708
PCT Pub. Date: Oct. 23, 2014

(65) Prior Publication Data
US 2016/0038599 A1    Feb. 11, 2016

Related U.S. Application Data

(60) Provisional application No. 61/854,108, filed on Apr. 18, 2013.

(51) Int. Cl.
*A61K 9/00*    (2006.01)
*A61K 47/36*   (2006.01)
(Continued)

(52) U.S. Cl.
CPC .......... *A61K 47/36* (2013.01); *A61K 9/0019* (2013.01); *A61K 9/0024* (2013.01); *A61K 47/61* (2017.08);
(Continued)

(58) Field of Classification Search
CPC .................................................... A61K 47/36
See application file for complete search history.

(56) References Cited

U.S. PATENT DOCUMENTS

2006/0258698 A1 * 11/2006 Mudumba ............ A61K 9/0019
514/291

FOREIGN PATENT DOCUMENTS

| WO | WO 0078285 A1    | 12/2000 |
| WO | WO 2011-014432 A1 | 2/2011 |
| WO | WO 2012-171335 A1 | 12/2012 |

OTHER PUBLICATIONS

International Search Report in International Application No. PCT/CN2014/000420, filed Apr. 17, 2014.

* cited by examiner

*Primary Examiner* — Paul Dickinson
(74) *Attorney, Agent, or Firm* — Saliwanchik, Lloyd & Eisenschenk

(57) ABSTRACT

The present invention provides compositions, and related kits and methods, for formation of hydrogels. The compositions comprise one or more chemically crosslinkable agents dissolved in an aqueous solution to form a precursor solution. The chemically crosslinkable agents useful in the present invention are selected from polymers modified with a molecule selected from acrylate, maleimide, vinylsulfone, N-hydroxysuccinimide, aldehyde, ketone, carbodiimide, carbonate, iodoacetyl, mercaptonicotinamide, quinone, thiol, amine, and combinations thereof. The precursor solution is characterized as being in an aqueous form at a non-physiologic physical-chemical condition and undergoing gelation when in contact with another fluid or body at a physiologic physical-chemical condition.

23 Claims, 6 Drawing Sheets

(51) Int. Cl.
  *A61L 27/52*   (2006.01)
  *A61K 49/04*   (2006.01)
  *C08B 15/00*   (2006.01)
  *C08B 37/16*   (2006.01)
  *C08B 37/02*   (2006.01)
  *C08B 37/08*   (2006.01)
  *C08B 37/00*   (2006.01)
  *C08L 1/28*   (2006.01)
  *C08L 5/02*   (2006.01)
  *C08L 5/04*   (2006.01)
  *C08L 5/08*   (2006.01)
  *C08L 5/16*   (2006.01)
  *A61K 47/61*   (2017.01)

(52) U.S. Cl.
  CPC ...... *A61K 49/0438* (2013.01); *A61K 49/0442* (2013.01); *A61L 27/52* (2013.01); *C08B 15/005* (2013.01); *C08B 37/0012* (2013.01); *C08B 37/0021* (2013.01); *C08B 37/0072* (2013.01); *C08B 37/0084* (2013.01); *C08L 1/286* (2013.01); *C08L 5/02* (2013.01); *C08L 5/04* (2013.01); *C08L 5/08* (2013.01); *C08L 5/16* (2013.01); *A61L 2400/06* (2013.01); *C08L 2205/02* (2013.01)

BIOCOMPATIBLE IN SITU HYDROGEL

CROSS-REFERENCE TO RELATED APPLICATIONS

This application is the U.S. national stage application of International Patent Application No. PCT/CN2014/000420, filed Apr. 17, 2014, which claims the benefit of U.S. Provisional Application Ser. No. 61/854,108, filed Apr. 18, 2013, which are hereby incorporated by reference in their entirety including any tables, figures, or drawings.

FIELD OF THE INVENTION

This disclosure generally relates to a material that can form a hydrogel upon injection into a space within the body, and applications thereof.

BACKGROUND

A hydrogel is a material consisting of water-filled networks of cross-linked polymers. One of the most important features of this type of material is its hydrophilic nature, which enables many of its varieties to be compatible with the body. Moreover, the physical and chemical properties, which include, but are not limited to, mechanical properties, volume change behavior, drug controlled release behavior, functionalization of chemical moieties, and gel-body interactions, can be well controlled in a hydrogel system. Therefore, a hydrogel is favorable in many kinds of biomedical applications, including, but not limited to, tissue engineering, tissue augmentation, tissue filling, drug delivery, and cell delivery.

However, a hydrogel is a viscoelastic solid, and due to its limited ability to deform, it is difficult to place into the body without surgically opening the body. A special type of hydrogel, sometimes referred to as "in situ" hydrogel, is a material that can change from a viscoelastic liquid to viscoelastic solid (or "sol-gel transition") when the gel is injected into the body. This property enables the material to be placed in the body by a minimally invasive manner, e.g., by an injection. This additional advantage, together with the other properties stated above, make in situ hydrogels attractive candidates in many biomedical applications. Nevertheless, the development of this type of hydrogel is challenging. One of the most challenging spaces to form an in situ hydrogel is the endoluminal space for endoluminal therapy. "Endoluminal" is an adjective describing a space inside the lumen of a body. A lumen refers to a tube-like structure inside the body. Examples of lumens in the body include, but are not limited to, blood vessels, lymphatic vessels, respiratory tract, digestive tract, fallopian tubes, and ductus deferens. One type of endoluminal therapy is to use an external material to fill up certain spaces inside the lumen. Examples of this type therapy include lumen embolization and ligature. The medical conditions needed for this type of therapy may be of various kinds. One particular example of a medical condition is vascular abnormality.

The prevalence and central role of vascular abnormality in various pathological conditions have been driving the biopharmaceutical industry to develop new medicines and devices. Efficient and secured occlusion of abnormal vessel segments has been one of the major, yet unmet, demands especially in the treatments of arteriovenous malformation (AVM), aneurysm and tumor. Compared with surgery and radiotherapy, endovascular embolization allows minimal invasiveness, less complications and shorter hospitalization. With the recent advancement in intervention equipment and materials, endovascular embolization has become the primary choice, or important adjunct, in clinical treatment of vascular pathology. Coils and liquid embolic systems are the two most popular embolic materials. A problem with coils is the incomplete initial occlusion (<50% of vascular cavities) and the consequent recanalization due to the inherent physical constraints of coil therapy. There are limited liquid embolizing agents available for clinical use. Toxicity and lack of control are the main drawbacks. For example, the most used embolizing agent, Onyx, is composed of ethylene vinyl alcohol (EVAL) copolymer dissolved in dimethyl sulfoxide (DMSO). To obliterate the abnormal vasculature, Onyx is injected through a guided micro catheter, and its main component, EVAL, immediately precipitates and solidifies upon the diffusion of DMSO, which is known to be toxic in liquid form. The quick gelation may result in adherence of the microcatheter to the embolic mass; thus, the procedure must be carefully conducted by experienced radiologists and vascular surgeons. Moreover, Onyx is non-adhesive to vessel walls, which brings high risk of gel migration during and after operation. The side effects, difficult manipulation and potential complication lead to increased healthcare cost and unsatisfactory outcome.

A potential drawback of forming chemically crosslinked in situ hydrogels in some applications is the brittleness of the gel. Hydrogels formed by chemical crosslinking alone can be brittle and easily broken down into pieces at relatively small stress and small deformation. For many applications where the hydrogel is expected to experience forces such as, for example, in endoluminal therapy and tissue augmentation, where forces always exist, or for drug delivery and cell delivery, where forces may possibly exist, the ability of gels to be able to withstand a large stress or large extent of deformation is desirable.

BRIEF SUMMARY

Aspects of the present invention provide compositions comprising one or more chemically crosslinkable agents dissolved in an aqueous solution. The composition is characterized by being in an aqueous form at non-physiologic physical-chemical conditions: at a pH lower than the pH of the body, at a temperature lower or higher than the temperature of the body, and/or in a non-buffered or slightly buffered solution. The composition is further characterized as undergoing chemical gelation when in contact with fluids and/or the body at a physiologic physical-chemical condition, e.g., a fluid/body of pH close to the body's pH, a fluid/body with a temperature close to the body's temperature and/or a fluid/body buffered similar to the body's buffer strength. The composition may also be characterized by being in an aqueous form at certain non-physiologic physical-chemical conditions, such as, e.g., temperature, pH, buffering capacity, ionic strength etc., that are different from the body's or body fluid's physiologic physical-chemical conditions, and further characterized as undergoing chemical gelation when in contact with one's body or body fluid.

Other aspects of the present invention provide compositions comprising one or more chemically crosslinkable agents dissolved in an aqueous solution to form a precursor solution, wherein the chemical reaction rate is higher at physiological conditions compared to non-physiological conditions. The precursor solution is characterized by being in an aqueous form at a pH that is different from the body's pH by at least about 0.5. The precursor solution is further characterized by being non-buffered or slightly buffered.

The precursor solution is further characterized as being in an aqueous form at a temperature lower or higher than one's body temperature by at least about 5 degrees Celsius. The precursor solution is further characterized as undergoing gelation when in contact with one's body or body fluid. In a preferred embodiment, the precursor solution is at a temperature about 2 to 15 degrees Celsius and a pH about 5 to 6 or about 8 to 9.

In some embodiments, at least one of the chemically crosslinkable agents are polymers modified with a molecule selected from conjugated unsaturated groups including acrylate, maleimide, vinylsulfone, quinone, etc.; an active ester, including N-hydroxysuccinimide, an aldehyde, a ketone, a carbodiimide, a carbonate, an iodoacetyl, a mercaptonicotinamide, and combinations thereof. In some embodiments, at least one of the chemically crosslinkable agents is from polymers modified with a molecule selected from a nucleophile, such as, for example, a thiol and a amine.

In one embodiment, the composition further comprises at least one of a physically crosslinkable agent and a viscosity modulating agent. In some embodiments, the physically crosslinkable agents are polymers that can be crosslinked by physical forces in solutions. Examples of such physical forces include ionic interaction, hydrophobic interaction, hydrogen bonding, and Van der Waals forces. Examples of polymers that can form ionic interactions include polymers that carry a critical density and certain spatial arrangement of negative charges, such as for example, alginate and gallan gum, that can be crosslinked by multivalent salts, such as for example $Ca^{2+}$, $Mg^{2+}$, $Na^{+}$, $Fe^{3+}$, $Al^{3+}$ etc. Examples of polymers that can form crosslinks by hydrophobic interaction include polymers carrying a critical density and certain arrangement of hydrophobic groups, such as for example Poly(N-isopropylacrylamide) and Pluronic F127. In some embodiments, the hydrophobicity of the hydrophobic groups of these agents may be increased and the physical crosslinks are increasingly formed when chemical crosslinks are formed. In some preferred embodiments, the hydrophobicity of these groups may be increased and the physical crosslinks are increasingly formed when these agents are injected to the body, when the agent encounters a change in the physical-chemical environment, including temperature, ionic strength, salt content and pH.

Examples of polymers that can form crosslinks by hydrogen bonding include polymers that carry a critical density and certain spatial arrangements of chemical groups containing H, O, N, C, S, F and alike, such as, for example, agarose and certain self-assembling poly-peptides and proteins. In some embodiments, the physical crosslinks are formed by a combination of different forces, such as in polymers including certain self-assembling polypeptides (e.g, AcN-Arginine-Alanine-Aspartate-Alanine-Arginine-Alanine-Aspartate-Alanine-Arginine-Alanine-Aspartate-Alanine-Arginine-Alanine-Aspartate-Alanine-$CNH_2$) and proteins (e.g., gelatin and collagen). In some preferred embodiments, physical crosslinking occurs after the physically crosslinkable agents are injected into the body. In some embodiments, the physical crosslinking is triggered by a change in physical-chemical environment, including temperature, ionic strength, salt content and pH, when the physically crosslinkable agent is injected into the body. In some embodiments, the physically crosslinkable agent is attached chemically to the chemically crosslinkable agent either before or after the injection. In some embodiments, one or more agent that facilitates the formation of physical crosslinks of the physically crosslinkable agent is present in the solution. Examples of these agents include calcium phosphate, or the alike, for alginate. In some embodiments, the viscosity modulating agent is a salt or a polymer that changes the viscosity of the aqueous solution. In some embodiments, the viscosity of the aqueous solution after modulation is 0.5 Centipoise to 100,000 Centipoise.

In one embodiment, at least one of the chemically crosslinkable polymer is a polysaccharide.

In one embodiment, the aqueous solution further comprises a salt, an organic solvent, a drug, an adhesion agent, and/or an imaging agent. In some embodiments, the drug, adhesion agent and/or imaging agent is conjugated on any of the chemically crosslinkable agents, physically crosslinkable agents, and viscosity modulating agents.

Additional aspects of the present invention provide methods of forming a hydrogel within a space in a body comprising: (i) injecting an aqueous solution comprising one or more chemically crosslinkable agent into the space, wherein the one or more chemically crosslinkable agent is selected from polymers modified with a molecule selected from acrylate, maleimide, vinylsulfone, N-hydroxysuccinimide, aldehyde, ketone, carbodiimide, carbonate, iodoacetyl, mercaptonicotinamide, quinone, thiol, amine, and combinations thereof, wherein the solution is in an aqueous form at a non-physiologic physical-chemical condition (e.g. temperature, pH, buffering capacity, ionic strength etc., that is different from the body's or body fluid's physical-chemical condition);

(ii) triggering the formation of a hydrogel within the space, the triggering occurring when the aqueous solution contacts the body and/or body fluid at a physiologic physical-chemical condition within the space; and (iii) allowing the forming of the hydrogel within the space.

In some embodiments, the forming of the hydrogel takes from 1 second to 2 hours. In some embodiments, the space in the body where the aqueous solution is injected is a lumen; in other embodiments, the space is a cavity. The resultant hydrogel may also serve to embolize the lumen or cavity. The concentration, degree of modification, polymer type, and reactive group type are considerations based on the rapidity of hydrogel formation desired.

Other aspects of the present invention provide methods of forming a hydrogel within a space in a body comprising: (i) injecting an aqueous solution comprising both chemically crosslinkable agents and physically crosslinkable agents; and (ii) allowing the forming of the hydrogel within the body or at the surface of the body.

In one embodiment, the chemical crosslinks are formed at a rate higher than the physical crosslinks. In another embodiment, the physical crosslinks are formed at a rate higher than the chemical crosslinks. In some embodiments, the forming of the hydrogel takes from 1 second to 2 hours. In some embodiments, the space in the body where the aqueous solution is injected is a lumen; in other embodiments, the space is a cavity; in other embodiments, the space is a defected site in the body. The resultant hydrogel may also serve to augment a cavity, a tissue or fill the defected site. In some embodiments the defected site may be a soft tissue or hard tissue.

Other aspects of the present invention provide methods of forming a hydrogel within a space in a body comprising: (i) injecting an aqueous solution comprising chemically crosslinkable agents, including a multi-vinylsulfone containing polymer and a multi-nucleophile containing polymer, into the space, wherein the solution is in an aqueous form at a pH of 6.5 or lower; at a temperature of 20 degree Celsius or lower; and/or when in a non-buffered solution; (ii) triggering the formation of a hydrogel within the space, the triggering occurring when the aqueous solution contacts a body or a body's buffered fluid of pH 7.2 or higher, and/or a temperature of 30 degree Celsius or higher; and (iii) forming the hydrogel within the space. In some embodiments, the forming of the hydrogel takes from 1 second to 2 hours. In some embodiments, the space in the body where the aqueous solution is injected is a lumen; in other embodiments, the space is a cavity. The resultant hydrogel may also serve to embolize the lumen or cavity. The concentration, degree of modification, polymer type, reactive group type, pH of the solution, buffering capacity of the solution, and temperature of the solution also needs to be designed for such rapid change.

In one embodiment, the forming of the hydrogel comprises covalently bonding the chemically crosslinkable polymers. In other embodiments, the forming of the hydrogel comprises physically bonding the physically crosslinkable agent. In other embodiments, the physically crosslinkable agent is chemically attached to the chemically crosslinkable agent before or after injection. In some embodiments, the degree of modification of the chemically crosslinkable polymers or the amount of chemical crosslinkers are carefully selected so that reactive groups that can potentially bind to a drug can be minimized. In some embodiments, the physically crosslinkable agent also serves to reduce the swelling of the hydrogel to minimize the volume enlargement effect and prevent enlargement of mesh size and drug diffusivity inside the gel.

In one embodiment, the aqueous solution further comprises at least one of a physically crosslinkable agent and a viscosity modulating agent.

In one embodiment, the triggering of the formation of the hydrogel further comprises a trigger by a change in temperature, ionic strength, salt composition, organic solvent content, water content, buffering capacity or a combination thereof, when the solution is in contact with the body fluid. In some embodiments, the change in temperature trigger comprises a temperature difference between the solution being injected, at a temperature below 10 degrees Celsius, and a body fluid, at a temperature between 25 and 45 degrees Celsius.

DETAILED DESCRIPTION

Figure 1:
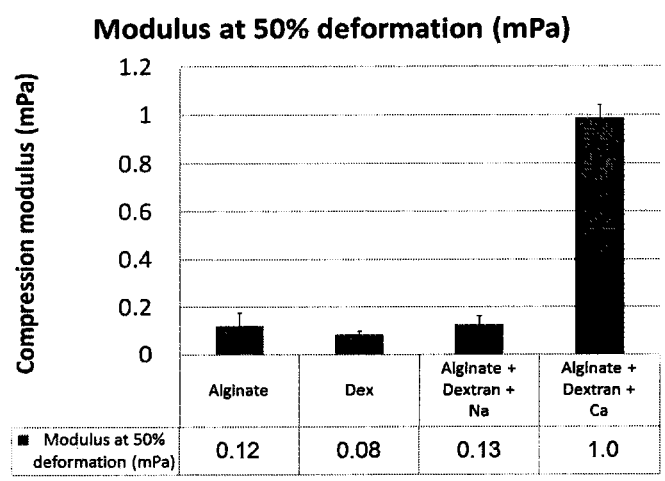
FIG. 1 shows a compression test on different hydrogel composed of physical crosslinkink alone, chemical crosslinking alone, or a combination of both types of crosslinks.

Aspects of the present invention are directed to compositions and related methods and kits that can form in situ hydrogels in physiological environments indicative of an animal body, such as, but not limited to, the human body.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, etc. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Prior to setting forth the invention in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

Definitions

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "hydrogel" describes a system of water soluble polymers, water insoluble cross linking points, and an aqueous solution that bathes the polymers. The components of the system can be viewed macroscopically as a unit. The water soluble polymers are cross linked by a chemical bond at the cross linking points so that the water soluble polymers are no longer soluble in the aqueous solution. Even though the cross linked polymers are no longer soluble in the aqueous solution, they are not precipitated from the aqueous solution, which allows the hydrogel to be able to hold a large volume of the aqueous solution while still maintaining its shape.

As used herein, the term "trigger" or "triggering" refers to an event that initiates the change of the polymer solutions of the present invention from a non-gelling to a gelling state. The physical and/or chemical aspects that initiate a triggering event are described herein and include changes in pH and/or temperature.

The present invention provides precursor, aqueous solutions for the formation of a hydrogel. The hydrogel can be formed at a space/site in the body from precursor molecules that are injected into the space/site as an aqueous solution. The precursor molecules, according to an embodiment, are two or more molecules that can facilitate formation of a hydrogel. The hydrogel must not cause an undesirable reaction in the body. Accordingly, the two or more precursor molecules must be biocompatible and non-immunogenic. Examples of biocompatible polymers whose derivatives can be utilized as precursor molecules include hyaluronic acid (HA), polyethylene glycol (PEG), dextran, carboxymethyl cellulose (CMC), polyvinyl alcohol (PVA), alginate, cyclodextran and the like.

Aspects of the present invention provide compositions comprising chemically crosslinkable agents dissolved in an aqueous solution to form a precursor solution. The composition is characterized by being in an aqueous form: at a pH lower than the pH of the body, at a temperature lower or higher than the temperature of the body, and/or in a non-buffered or slightly buffered solution (i.e., non-physiologic physical-chemical conditions). The composition is further characterized as undergoing chemical gelation when the precursor solution is in contact with a fluid of pH close to the body's pH, a fluid with a temperature close to the body's temperature and/or a fluid buffered similar to the body's buffer strength (i.e., physiologic physical-chemical conditions). The composition may also be characterized by being in an aqueous form at certain non-physiologic physical-chemical conditions, such as, e.g., temperature, pH, buffering capacity, ionic strength etc., that are different from the body's or body fluid's physical-chemical conditions, and further characterized as undergoing chemical gelation when in contact with one's body or body fluid.

In an embodiment, the chemically crosslinkable agents include one or more biocompatible polymer molecules modified with multiple vinylsulfone groups (multi-vinylsulfone molecule, P-VS) and one or more polymer molecules modified with multiple nucleophiles (multi-nucleophile molecule, P-Nu). The P-VS can be, for example, a hydroxyl-bearing biocompatible polymer modified with at least two functional vinylsulfone groups. The vinylsulfone groups can be linked to the hydroxyl group. Examples of other nucleophiles useful in aspects of the present invention include thiols and amines, which can be added to a biocompatible polymer. Likewise, in place of multiple vinylsulfone groups, multiple groups of the following may be utilized in aspects of the present invention: acrylate, maleimide, N-hydroxysuccinimide, quinone, aldehyde, ketone, carbodiimide, carbonate, iodoacetyl, mercaptonicotinamide.

When the P-VS and the P-Nu are mixed in an aqueous solution (e.g., non-buffered water) and contacted with a fluid of a particular pH range, a hydrogel is formed. The vinylsulfone groups are chemically reactive with the nucleophile groups. For example, the vinylsulfone groups can covalently bond to the nucleophile groups to facilitate formation of the hydrogel.

VS can react very rapidly with a nucleophile like thiol (SH), at proper pH, temperature, ionic strength, etc. By carefully selecting the physical chemical properties of the polymer, one can control the gelation time of the polymer. For applications that require fast gelation, the selection of material properties includes, but is not limited to, increasing molecular weight, increasing the degree of modification, using a bulky polymer having a relatively large radius of gyration at relatively low molecular weight, using a non-charged polymer, and/or increasing polymer concentration.

The chemically crosslinkable agents can dissolve in a biocompatible solution (e.g., water, physiological saline, or the like) to form the aqueous solution. For example, the solution can have a physiological pH of about 5.3. The aqueous solution can also include a salt, a solvent, any other molecule that regulates the pH of the solution, any other molecule that facilitates modification of the precursor polymer, and therapeutic molecule, or any other molecule that minimizes the potential hazard when the chemically crosslinkable agents or the hydrogel are used in a biological system. The aqueous solution is a solution before gelation so that it can be easily injected to the site/space.

Other aspects of the present invention provide compositions comprising one or more chemically crosslinkable agents dissolved in an aqueous solution to form a precursor solution, wherein the chemically crosslinkable agents are selected from polymers modified with a molecule selected from acrylate, maleimide, vinylsulfone, quinone, N-hydroxysuccinimide, aldehyde, ketone, carbodiimide, carbonate, iodoacetyl, mercaptonicotinamide, and combinations thereof. The composition is characterized by being in an aqueous form: at a pH lower than the pH of the body, at a temperature lower or higher than the temperature of the body, and/or in a non-buffered or slightly buffered solution. The composition is further characterized as undergoing chemical gelation when the precursor solution is in contact with a fluid of pH close to the body's pH, a fluid with a temperature close to the body's temperature and/or a fluid buffered similar to the body's buffer strength. The composition may also be characterized by being in an aqueous form at certain physical-chemical conditions, such as, e.g., temperature, pH, buffering capacity, ionic strength etc., that are different from the body's or body fluid's physical-chemical conditions, and further characterized as undergoing chemical gelation when in contact with one's body or body fluid. For example, and in no way limiting, the precursor solution is characterized by being in an aqueous form at a pH of 6 or lower and further characterized as undergoing gelation when in contact with a fluid of pH of 7 or higher.

The precursor molecules can include polymers that are biocompatible and non-immunogenic (e.g., do not react with biomolecules, cells, tissues, or the like, related to the injection). Examples of biocompatible polymers whose derivatives can be utilized as precursor molecules include hyaluronic acid (HA), polyethylene glycol (PEG), dextran, carboxymethyl cellulose (CMC), polyvinyl alcohol (PVA), alginate, cyclodextran, and the like. In an embodiment, the precursor molecules can be P-VS and P-Nu, as described above. The aqueous solution can also include a biocompatible buffer solution (e.g., water, PBS, etc.), a salt, an aqueous solvent, any other molecule that regulates the pH of the solution, any other molecule that facilitates modification of the precursor polymer, and therapeutic molecule, or any other molecule that minimizes the potential hazard when the precursors or the hydrogel are used in a biological system.

In one embodiment, the composition further comprises at least one of a physically crosslinkable agent and a viscosity modulating agent. In some embodiments, the physically crosslinkable agents are polymers that can be crosslinked by physical forces in solutions. Examples of the physical forces include ionic interaction, hydrophobic interaction, hydrogen bonding, and Van der Waals forces. Examples of polymers that can form ionic interactions include polymers that carry a critical density and certain spatial arrangement of negative charges such as, for example, alginate and gallan gum; and polymers that can be crosslinked by multivalent salt such as, for example, $Ca^{2+}$, $Mg^{2+}$, $Na^+$, $Fe^{3+}$, $Al^{3+}$ etc. Examples of polymers that can form crosslinks by hydrophobic interaction include polymers carrying a critical density and certain arrangement of hydrophobic groups such as, for example, Poly(N-isopropylacrylamide) and Pluronic F127. In some embodiments, the hydrophobicity of the hydrophobic groups of these agents may be increased and the physical crosslinks are increasingly formed when chemical crosslinks are formed. In some preferred embodiments, the hydrophobicity of these groups may be increased and the physical crosslinks are increasingly formed when these agents are injected into the body, and when the agent encounters a change in the physical-chemical environment, including temperature, ionic strength, salt content and pH. Examples of polymers that can form crosslinks by hydrogen bonding include polymers that carry a critical density and certain spatial arrangements of chemical groups containing H, O, N, C, S, F and alike such as, for example, agarose and certain self-assembling poly-peptides and proteins. In some embodiments, the physical crosslinks are formed by a combination of different forces such as, for example, in polymers including certain self-assembling polypeptides (for example AcN-Arginine-Alanine-Aspartate-Alanine-Arginine-Alanine-Aspartate-Alanine-Arginine-Alanine-Aspartate-Alanine-Arginine-Alanine-Aspartate-Alanine-$CNH_2$) and proteins (e.g., gelatin and collagen). In some preferred embodiments, the physical crosslinking occurs after the physically crosslinkable agents are injected to the body. In some embodiments, the physical crosslinking is triggered by a change in the physical-chemical environment including temperature, ionic strength, salt content and pH, when the physically crosslinkable agent is injected to the body.

In some embodiments, the physically crosslinkable agent is attached chemically to the chemically crosslinkable agent either before or after the injection. In some embodiments, an agent that facilitates the formation of the physical crosslinks of the physically crosslinkable agent is present in the solution. Examples of these agents include calcium phosphate, or alike, for alginate. In some embodiments, the viscosity modulating agent is a salt or a polymer that changes the viscosity of the aqueous solution. In some embodiments, the viscosity of the aqueous solution after modulation is 0.5 Centipoise to 100000 Centipoise.

In one embodiment, at least one of the chemically crosslinkable agents is a polysaccharide. In some embodiments, the chemically crosslinkable agent is a thiolated polymer.

In one embodiment, the aqueous solution further comprises a salt, an organic solvent, a drug and/or an imaging agent. In some embodiments, the drug and/or imaging agent is conjugated on any of the chemically crosslinkable agents, physically crosslinkable agent, and viscosity modulating agent.

Other aspects of the present invention provide methods of forming a hydrogel within a space in a body comprising: (i) injecting an aqueous solution comprising one or more chemically crosslinkable agent into the space, wherein the chemically crosslinkable agent is selected from polymers modified with a molecule selected from acrylate, maleimide, vinylsulfone, quinine, N-hydroxysuccinimide, aldehyde, ketone, carbodiimide, carbonate, iodoacetyl, mercaptonicotinamide, thiol, amine and combinations thereof, wherein the solution is in an aqueous form at a non-physiologic physical-chemical condition, e.g. temperature, pH, buffering capacity, ionic strength etc., that is different from the body's or body fluid's physical-chemical condition; (ii) triggering the formation of a hydrogel within the space, the triggering occurring when the aqueous solution contacts a body or a body fluid within the space; and (iii) forming the hydrogel within the space. In some embodiments, the forming of the hydrogel takes from 1 second to 2 hours. In some embodiments, the space in the body where the aqueous solution is injected is a lumen; in other embodiments, the space is a cavity. The resultant hydrogel may also serve to embolize the lumen or cavity. In some embodiments, a physically crosslinkable agent is attached chemically to the chemically crosslinkable agent either before or after the injection. The concentration, degree of modification, polymer type, and reactive group type are considerations based on the rapidity of hydrogel formation desired.

In some embodiments, the aqueous solution used to dissolve the polymers is a physiological saline; the pH of physiological saline is 5.3 and is non-buffered. The non-buffered condition allows rapid pH rise after the polymer solution encounters a buffered body fluid with a typical pH of about 7.4.

In one embodiment, the aqueous solution further comprises at least one of a physically crosslinkable agent and a viscosity modulating agent.

In one embodiment, the forming of the hydrogel comprises covalently bonding the chemically crosslinkable agent(s). In other embodiments, the forming of the hydrogel comprises physically bonding the physically crosslinkable agents.

In one embodiment, the triggering of the formation of the hydrogel further comprises a trigger by a change in temperature, ionic strength, salt composition, organic solvent content, water content, or a combination thereof, when the solution is in contact with the body fluid. In some embodiments, the change in temperature trigger comprises a temperature difference between the solution being injected, having a temperature below 10 degree Celsius, and a body fluid, having a temperature between 25 and 45 degrees Celsius.

The chemical crosslinking reaction, or the chemical gelation, of the chemically crosslinkable agent(s) is triggered by a change in physical and/or chemical conditions. For example, one possible combination of chemically crosslinkable agents includes VS and SH containing polymers. VS can react with SH rapidly at physiological pH, but it will not react with SH when the pH is low, e.g. at the pH of normal saline of about pH 5.5. In one aspect of this embodiment, the precursors were dissolved in a solution of low pH, e.g. normal saline of pH 5.5. After the solution is injected into the body, the pH will increase to about 7.4. The rapid reaction between VS and SH at this physiological pH will then stop the polymer from being diluted in the body and the precursor solution can form a hydrogel. For another example, the reaction kinetics between VS and SH is not as high when the solution is at low temperature as at physiological temperature. In one aspect of this embodiment, the precursor solution is cooled to a lower temperature. When the solution is injected into the body, the temperature increases to about 37 degrees Celsius and the rapid reaction between VS and SH will then stop the polymer from being diluted in the body and the precursor solution can form a hydrogel. However, it should be noted that these embodiments do not exclude the use of a combination of physical and chemical triggers, for example, pH and temperature triggers, to control the formation of a hydrogel in the body. The advantages of triggered chemical gelation include, but are not limited to, much faster gelation, more controllable physical properties (e.g. mechanical properties) and more durable hydrogels.

For applications in most parts of the body, the gelation condition should be at a mild physiological condition. The physiological condition should consist of an aqueous condition, a pH about 6.5 to 7.8, a temperature about 36 to 42 degrees Celsius, a salt concentration about similar to 0.9% sodium chloride, etc.

Many spaces inside the body are either rich with aqueous fluids (e.g., body fluid) or can be easily filled with aqueous fluids (or body fluid) when a foreign body, e.g. the solution being injected, is sensed by the body. This requires the hydrogel to be able to form relatively fast, or the solution be relatively viscous, when the solution is injected into the body.

Many spaces inside the body are filled with aqueous fluids that flow, for example in the blood vessels. If an in situ hydrogel needs to be applied in these spaces, the gelation should be fast enough to overcome the dilution effect, and the force resistance to flow, e.g. the viscosity or some hydrophobic interaction between polymers, should be high enough to overcome the dilution effect.

Also, many spaces inside the body that are rich in flowing aqueous fluids are very small, such as for example, a blood or lymphatic vessel. This requires the material to be injectable from an even smaller needle or catheter. Also, the material injected cannot be too difficult to deform, e.g. in the case of a week gel, gel particle solution, or very viscous material.

Furthermore, many spaces inside the body that are rich in flowing aqueous fluids are very small and buried deep in the body, such as for example, a blood or lymphatic vessel in the brain. This requires the catheter to be long enough to reach the site. A long catheter implies a long travelling distance of the material, so if the material gels rapidly in an uncontrollable manner, the catheter used to transport the material to the distal location can be easily clogged. In one embodiment, the present invention controls the gelation so that the solidification occurs after the material is injected out of the catheter.

In some embodiments, the invention may include a viscosity modulating agent. "Viscosity" describes the ability of a fluid material to resist gradual deformation by a stress. By definition, the gel precursor polymer solution is a viscoelastic liquid, which means that before it forms a gel, which is a viscoelastic solid, it will be continuously deformed when a stress is applied, and the ease of this deformation is governed by the viscosity of the solution. In the body where the compositions and methods of the present invention are being applied, such stress inevitably exists to certain degrees in various locations. The stress in the body may include, but is not limited to, the following: stress from movement of solid, e.g. movement of muscles; and stress from movement of liquid, e.g. movement of body fluid such as blood. The movement of a solid will destroy the shape of the gel precursor, whereas the movement of liquid will both destroy the shape and affect the concentration of gel precursors. For example, if the invention is being used in a relatively stable location, including but not limited to, under skin, the stress may be low because a person can be asked to not move for a certain period of time to avoid stress of muscle movement. Also, the space may be in a relatively dry location, or the space may have limited liquid movement. In this space, the gel formation can be purely controlled by elapse of time, which means, one can control "when" to inject a gel precursor into the body so that the gel forms within a reasonable time after injection, such as for example, 5 minutes after injection. The viscosity of the polymer solution in this case can be relatively low. In another example, if the invention is being used in a relatively dynamic location, including but not limited to, around heart muscle or inside a blood vessel, the stress from the movement of muscle or liquid may be large. In this case, a more viscous solution may be favored. The viscosity modulation agent in the invention allows one to finely tailor the invention to different applications, such as for example, using a relatively fast reacting VS/SH polymer in solution of relatively high viscosity for endovascular embolization.

In yet still another embodiment, the invention may include a physically crosslinkable agent. A hydrogel can be brittle if only chemical crosslinking is presented. For certain applications, the hydrogel that is formed may have to bear relatively high loads that may cause the resultant hydrogel to break apart. Examples of the locations of gel injection in the body that may experience high load of stress includes, but is not limited to, inside a blood vessel, under the skin, under a muscle, as part of the bone, between cartilage, as a part of cartilage, at the joints, etc. A crosslinked physically crosslinkable agent, e.g. a physically crosslinkable polymer, when forming in the presence of a hydrogel network formed by a chemically crosslinkable agent, can help to increase the load bearing capacity of the gel. An important aspect of this invention is characterized by the injection of an aqueous solution, not a gel, gel particle or gel slurry, into the body such that the formation of both physical and chemical crossslinks are only completed after the injection. The gel formation may be first caused by the chemical crosslinks between chemically crosslinkable agents and followed by a physical crosslinking between physically crosslinkable agents, or first by physical crosslinks by the physically crosslinkable agents and followed by a chemical crosslinking between chemically crosslinkable agents, before the physical crosslinks. In some applications, the two crosslinking reactions, or interactions, may happen at similar rate. In some embodiments, either one or both of the chemical and physical crosslinks are trigger by a change in a physical-chemical environment, e.g. temperature, ionic strength, salt composition, organic solvent content, water content, or a combination thereof, when the solution is in contact with the body fluid. Examples of physically crosslinkable agents that can form physical crosslinks when encountering the body including Poly(N-isopropylacrylamide), Pluronic F127, certain polypeptides (e.g., AcN-Arginine-Alanine-Aspartate- Alanine-Arginine-Alanine-Aspartate-Alanine-Arginine-Alanine-Aspartate-Alanine-Arginine-Alanine-Aspartate-Alanine-$CNH_2$) and proteins. The combination of the chemical crosslinks and the physical crosslinks can enable the formed hydrogel to be resistance to stress. The presence of some physically crosslinkable agents, e.g., alginate, gellan gum, gelatin, collagen, and certain peptides, may also help to promote cell adhesion, wound healing, prevent surgical adhesion, stop bleeding etc. or a combination of these effects.

In yet another embodiment, the physical crosslinkable agent is triggered by a change in physical and chemical conditions. In other words, the embodiment describes a triggered physical gelation in addition to a chemical gelation.

In another embodiment, the physically crosslinkable agent may be located on the chemically crosslinkable polymers. The physical crosslinks here refer to any physical interaction between two polymers, including hydrogen bonding, ionic interaction, hydrophobic interaction, and Van de Waals forces. As previously described herein, for certain applications, resistance to stress is a favorable property of the formed in situ hydrogels. A chemically crosslinkable polymer bearing one or more physically crosslinkable groups can help the polymer remain resistant to stress while delaying or preventing the gradual dissolution of the physically crosslinkable agents to the surrounding environment.

In yet another embodiment, the aqueous solution that the gel precursors are dissolved in contains one or more drug, imaging agent or other molecules. Hydrogels are known for the ability to control the release of molecules by controlling the mesh size or the crosslinking density. However, historically this is difficult to achieve for in situ hydrogels because the dynamic environment in the body often greatly affects the designed crosslinking properties. Because the compositions, kits, and methods of the present invention have the ability to control gelation in very harsh environments in the body, one can achieve encapsulation or controlled release of various chemical agents, including drugs or imaging molecules, in a well-controlled manner. For example, a radiocontrast agent can be mixed in the precursor solution to be used in embolization of a vessel, so that the precursor can be visible, and the positioning of the gel can be guided with imaging devices. Also, for example, an anti-cancer drug can be mixed in the precursor solution to be used in embolizing blood vessels around tumors so that the tumor can be suppressed by both elimination of nutrient support and the effect of the anti-cancer drug.

In yet another embodiment, a molecule that is interactive in the body can be conjugated to the polymer in the precursor solution of the gel. The type of interaction between this type of molecule and the body includes, but is not limited to, adhesion, anti-adhesion, promotion of growth, inhibition of growth, prevention of bleeding, promotion of wound healing, promotion of blood clotting, and curing or treatment of a disease. The present invention can achieve this by chemically conjugating different molecules onto the polymers in the precursor solution, or chemically modifying the polymers in the precursor solution. For example, some peptides are known to be adhesive to a certain part of the body. For example, by conjugating these peptides to a VS containing polymer by simple click chemistry, one can modify the surface properties of the hydrogel. For another example, a radiocontrast agent can be conjugated to the polymer so that the material is visible under radiological examination. For yet another example, a drug can be conjugated to the polymer for the purpose of curing and/or treating diseases. It should be noted that the choice of polymer for this conjugation may be a chemically crosslinkable agent, a physically crosslinkable polymer, or a viscosity modulating polymer.

In another aspect, the present invention provides kits for forming a hydrogel within a space in a body. The kit can include a first component comprising one or more chemically crosslinkable agent, wherein the chemically crosslinkable agent is selected from polymers modified with a molecule selected from acrylate, maleimide, vinylsulfone, quinine, N-hydroxysuccinimide, aldehyde, ketone, carbodiimide, carbonate, iodoacetyl, mercaptonicotinamide, thiol, amine, quinine, and combinations thereof. In some embodiments, the kit may include a second component comprising an aqueous solution. The kits may further include instructions for use thereof. The components of the kit may be provided as separate components, or one or more of the components may be provided pre-mixed. Furthermore, the first component may be provided in lyophilized form for mixing with the second component (aqueous solution) prior to use. In additional embodiments, the first component may be provided in solution, for mixing with the second component (aqueous solution) prior to use. In a further embodiment, the first component may be provided in multiple solutions (sub components), each containing one of the one or more chemically crosslinkable agents, for mixing with each other prior to use.

In some embodiments, the hydrogel is non-degradable. This means the none of the chemically crosslinkable agents, physically crosslinkable agents or viscosity modulating agents are degradable. For certain applications, for example, embolization of AVM (arteriovenous malformation), a non-degradable hydrogel is preferred.

In some embodiments, the hydrogel is partially degradable. This means the viscosity modulating agent and/or one of the crosslinkable agents, such as either of the chemically crosslinkable agents or physically crosslinkable agents, are degradable. The partial degradation of gel may be caused by the dissolution of the viscosity modulating agent and/or physically crosslinkable agent to the surrounding tissue. In some embodiments, the hydrogel is degradable. This means the viscosity modulating agent and/or both of the crosslinkable agent, such as either of the chemically crosslinkable agents or physically crosslinkable agents, is degradable. The degradation of gel may also be caused by the dissolution of the viscosity modulating agent and/or physically crosslinkable agent to the surrounding tissue, and the degradation of the chemically crosslinkable agent(s). The degredation of any of the viscosity modulating agents, chemically crosslinkable agents and physically crosslinkable agents may be caused by enzymatic degradation, hydrolysis, light, heat, electric, magnatic, interaction with a molecule, or the combination of the above. The degradability may be a preferred property for the hydrogel for tissue engineering, drug delivery, cell delivery, wound healing, tissue sealant, anti-adhesion for surgery, etc.

Thus, the following non-limiting embodiments are provided:

1. A composition comprising:
   one or more chemically crosslinkable agent containing polymer dissolved in an aqueous solution, wherein the composition is in an aqueous form at a non-physiologic physical-chemical condition, wherein the composition undergoes chemical gelation when in contact with a body or body fluid at a physiologic physical-chemical condition.

2. The composition of embodiment 1, further comprising a physically crosslinkable agent.

3. The composition of embodiment 1, further comprising a viscosity modulating agent, 4. The composition of embodiment 1, further comprising at least one of a physically crosslinkable agent and a viscosity modulating agent.

5. The composition of embodiment 1, wherein the one or more chemically crosslinkable agent is a polysaccharide.

6. The composition of any of embodiments 1, 2, 3, and 4, wherein at least one of the one or more chemically crosslinkable agent is a thiolated polymer.

7. The composition of any of embodiments 3, 4 and 6, wherein the viscosity modulating agent is a salt or a polymer that changes the viscosity of the aqueous solution.

8. The composition of any of embodiments 3, 6, and 7, wherein the viscosity of the aqueous solution after modulation is 0.5 Centipoise to 100000 Centipoise.

9. The composition of any of embodiments 1-8, wherein the aqueous solution further comprises a salt, an organic solvent, a drug and/or an imaging agent.

10. The composition of embodiment 9, wherein the drug and/or imaging agent is conjugated on any of the one or more chemically crosslinkable agent, physically crosslinkable agent, and viscosity modulating agent.

11. The composition of any embodiments 1-10, wherein the chemically crosslinkable agent comprises a polymer selected from hyaluronic acid, polyethylene glycol, dextran, carboxymethyl cellulose, polyvinyl alcohol, alginate, cyclodextran, and combinations thereof.

12. A method of forming a hydrogel within a space in a body, comprising:

injecting an aqueous solution comprising a chemically crosslinkable agent into the space, wherein the solution is in an aqueous form at a physical-chemical condition that is different from the physiologic physical-chemical condition in the space in the body;

triggering the formation of a hydrogel within the space, the triggering occurring when the aqueous solution contacts the body and/or a body fluid within the space; and allowing the hydrogel to form within the space.

13. The method of embodiment 12, wherein the forming of the hydrogel comprises covalently bonding the one or more chemically crosslinkable agents.

14. The method of any of embodiments 12-13, wherein the aqueous solution further comprises at least one of a physically crosslinkable agent and a viscosity modulating agent.

15. The method of embodiment 14, wherein the forming of the hydrogel comprises physically bonding the physically crosslinkable agent.

16. The method of any of embodiments 12-15, wherein the triggering of the formation of a hydrogel further comprises a trigger by a change in temperature, ionic strength, salt composition, organic solvent content, water content, or a combination thereof, when the solution is in contact with the body and/or body fluid.

17. The method of embodiment 16, wherein the change in temperature trigger comprises a temperature difference between the solution being injected, at a temperature below 10 degree Celsius, and a body fluid, at a temperature between 25 and 45 degrees Celsius.

18. The method of any of embodiments 12-17, wherein the forming of the hydrogel takes 1 second to 2 hours.

19. The method of any of embodiments 12-18, wherein the space in the body is a lumen in the body.

20. The method of any of embodiments 12-18, wherein the space in the body is a cavity in the body.

21. A composition comprising:

one or more chemically crosslinkable agent dissolved in an aqueous solution to form a precursor solution, wherein the one or more chemically crosslinkable agent is selected from polymers modified with a molecule selected from acrylate, maleimide, vinylsulfone, N-hydroxysuccinimide, aldehyde, ketone, carbodiimide, carbonate, iodoacetyl, mercaptonicotinamide, quinone, thiol, amine, and combinations thereof, wherein the precursor solution is in an aqueous form at a non-physiologic physical-chemical condition, wherein the precursor solution undergoes chemical gelation when in contact with a body or body fluid at a physiologic physical-chemical condition.

22. A method of forming a hydrogel within a space in a body, comprising:

(i) injecting an aqueous solution comprising one or more chemically crosslinkable agent into the space, wherein the one or more chemically crosslinkable agent is selected from polymers modified with a molecule selected from acrylate, maleimide, vinylsulfone, N-hydroxysuccinimide, aldehyde, ketone, carbodiimide, carbonate, iodoacetyl, mercaptonicotinamide, quinone, thiol, amine, and combinations thereof, wherein the solution is in an aqueous form at a non-physiologic physical-chemical condition;

(ii) triggering the formation of a hydrogel within the space, the triggering occurring when the aqueous solution contacts the body and/or body fluid at a physiologic physical-chemical condition within the space; and (iii) allowing the hydrogel to form within the space.

23. A kit for forming a hydrogel within a space in a body, comprising:

one or more first components comprising one or more chemically crosslinkable agents, wherein the one or more chemically crosslinkable agents are selected from polymers modified with a molecule selected from acrylate, maleimide, vinylsulfone, N-hydroxysuccinimide, aldehyde, ketone, carbodiimide, carbonate, iodoacetyl, mercaptonicotinamide, quinone, thiol, amine and combinations thereof; and a second component comprising an aqueous solution.

24. The kit of embodiment 23, further comprising instructions for use thereof.

All patents, patent applications, provisional applications, and publications referred to or cited herein are incorporated by reference in their entirety, including all figures and tables, to the extent they are not inconsistent with the explicit teachings of this specification.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. The data described herein merely illustrates examples of how to adjust the hydrogel properties for different applications. The choices of materials, cell lines, model animals, as well as the detailed experimental procedures, such as pH, osmolality and the like, are merely illustrations. All parts or amounts, unless otherwise specified, are by weight.

All percentages are by weight and all solvent mixture proportions are by volume unless otherwise noted.

Example 1: Triggered Chemical Gelation of Multi-Vinylsulfone Containing Polymer and Multi-Nucleophile Containing Polymer Vinylsulfonated dextran (dex-VS) of molecular weight (MW) 70 kDa and 8% degree of modification (DM), thiolated dextran (dex-SH) of MW 70 kDa and 8% DM, were dissolved in water or normal saline at 25% concentration. The water or normal saline in this area of the world (Hong Kong) has a pH around 5.3 to 5.5. The polymer solutions were mixed and loaded to a syringe. A 30 gauged needle was attached on the syringe and the solution was injected into PBS. A gel was formed shortly after the polymer solution encountered the PBS.

Example 2: Triggered Chemical Gelation of Multi-Vinylsulfone Containing Polymer and Multi-Nucleophile Containing Polymer Dex-VS of MW 70 kDa and 8% DM, dex-SH of MW 70 kDa and 8% DM, were dissolved in water or normal saline at 25% concentration. The water or normal saline in this area of the world (Hong Kong) has a pH around 5.3 to 5.5. The polymer solutions were mixed and loaded to a syringe. A 30 gauged needle was attached on the syringe and the solution was injected into 0.1 M phosphate buffer (PB). A gel was formed shortly after the polymer solution encountered the PB.

In another example, HA-VS of MW 29 kDa and 20% DM is dissolved in a buffered solution of pH 7 at 10% w/v, HA-SH of MW 29 kDa and 20% DM is dissolved in a buffered solution of pH 7.8 at 10% w/v. The two polymer is cooled on ice and mixed on ice. The solution was injected to PBS at 37 degree Celsius. A hydrogel is formed shortly after solution encounters the PBS.

Example 3: Triggered Chemical Gelation of Multi-Vinylsulfone Containing Polymer and Multi-Nucleophile Containing Polymer Dex-VS of MW 70 kDa and 8% DM, dex-SH of MW 70 kDa and 8% DM, were dissolved in water or normal saline at 25% concentration. The water or normal saline in this area of the world (Hong Kong) has a pH around 5.3 to 5.5. The polymer solutions were mixed and loaded to a syringe. A 30 gauged needle was attached on the syringe and the solution was injected into rabbit blood. A gel was formed shortly after the polymer solution encountered the blood.

Example 4: Triggered Chemical Gelation of Multi-Vinylsulfone Containing Polymer and Multi-Nucleophile Containing Polymer and a Viscosity Modulating Agent Vinylsulfonated HA (HA-VS) of MW 29 kDa and 25% DM were dissolved in PBS at 12% concentration, dex-SH of MW 40 kDa and 20% DM were dissolved in PBS at 25% concentration. The HA-VS acted as both chemical gelling agent and a viscosity modulation agent. The two polymer solutions, needle and syringe were placed on ice. After mixing the two polymer solutions, the cooled mixture were aspirated by the cooled syringe and injected to 37 degrees Celsius PBS solution. A gel was formed shortly after the polymer solution encountered the PBS.

Example 5: Triggered Chemical Gelation of Multi-Vinylsulfone Containing Polymer and Multi-Nucleophile Containing Polymer and a Viscosity Modulating Agent Vinylsulfonated HA (HA-VS) of MW 29 kDa and 25% DM were dissolved in PBS at 12% concentration, dex-SH of MW 40 kDa and 20% DM were dissolved in PBS at 25% concentration. The HA-VS acted as both chemical gelling agent and a viscosity modulation agent. The two polymer solutions, needle and syringe were placed on ice. After mixing the two polymer solutions, the cooled mixture were aspirated by the cooled syringe and injected to a rabbit eye. A gel was formed shortly after the polymer solution is injected to the eye.

Example 6: Triggered Chemical Gelation of Multi-Vinylsulfone Containing Polymer, Multi-Nucleophile Containing Polymer and a Physically Crosslinkable Agent Dex-VS of MW 70 kDa and 12% DM, dex-SH of MW 70 kDa and 12% DM, were dissolved in water or normal saline at 25% concentration. The water or normal saline in this area of the world (Hong Kong) has a pH around 5.3 to 5.5. Because the VS and SH are relatively hydrophobic chemical moieties, higher loading of these groups on the polymer will decrease the solubility of the polymer and make them easier to aggregate. In this example the dex-VS and dex-SH are both chemically crosslinkable polymer and physically crosslinkable polymer. The polymer solutions were mixed and loaded to a syringe. A 30 gauged needle was attached on the syringe and the solution was injected into PBS. An opaque gel was formed shortly after the polymer solution encountered PBS.

Example 7: Triggered Chemical Gelation of Multi-Vinylsulfone Containing Polymer, Multi-Nucleophile Containing Polymer, a Physically Crosslinkable Agent and a Viscosity Modulation Agent Dex-VS of MW 70 kDa and 12% DM, dex-SH of MW 70 kDa and 12% DM, were dissolved in a hyaluronic acid (HA) solution at 25% concentration. The HA solution contains 1.5% concentration of 1.5 mDa HA in water or normal saline. The water or normal saline in this area of the world (Hong Kong) has a pH around 5.3 to 5.5. Because the VS and SH are relatively hydrophobic chemical moieties, higher loading of these groups on the polymer will decrease the solubility of the polymer and make them easier to aggregate. In this example the dex-VS and dex-SH are both chemically crosslinkable polymer and physically crosslinkable polymer. HA in this example is the viscosity modulation agent. The polymer solutions were mixed and loaded to a syringe. A 30 gauged needle was attached on the syringe and the solution was injected into PBS. An opaque gel was formed shortly after the polymer solution encountered PBS.

Example 8: Triggered Chemical Gelation of Multi-Vinylsulfone Containing Polymer, Multi-Nucleophile Containing Polymer, a Physically Crosslinkable Agent and a Viscosity Modulation Agent Dex-VS of MW 70 kDa and 12% DM, dex-SH of MW 70 kDa and 12% DM, were dissolved in a alginate solution at 25% concentration. The alginate solution contains 1.5% concentration of alginate in water or normal saline. The water or normal saline in this area of the world (Hong Kong) has a pH around 5.3 to 5.5. Because the VS and SH are relatively hydrophobic chemical moieties, higher loading of these groups on the polymer will decrease the solubility of the polymer and make them easier to aggregate. The alginate solution can form hydrogle when it encountered divalent ions like calcium ions. In this example the dex-VS and dex-SH are both chemically crosslinkable polymer and physically crosslinkable polymer. Alginate is both the viscosity modulation agent and physically crosslinkable agent. The polymer solutions were mixed and loaded to a syringe. A 30 gauged needle was attached on the syringe and the solution was injected into PBS containing calcium ions. An opaque gel was formed shortly after the polymer solution encountered PBS.

Example 9: Gelation of Multi-Vinylsulfone Containing Polymer and Multi-Nucleophile Containing Polymer after a Time Elapses Dex-VS of MW 70 kDa and 8% DM, dex-SH of MW 70 kDa and 8% DM, were dissolved in PBS separately at 20% concentration. A gel was formed shortly after mixing the two polymers.

To control the gelation time, the pH of PBS was adjusted to 6.5, 7 and 7.4. The fastest gelation happed in pH 7.4. A pH 6.5 caused the gelation to slow down to about 5 minutes.

Another way to control the gelation time is to change the concentration of the polymer. When the polymer concentration decreased from 20% to 10%, the gelation time extended to about 13 minutes.

Another way to control the gelation time is to change the molecular weight of the polymer. When the MW of dextran was decreased to 40 kDa, the gelation time increased.

Another way to control the gelation time is to include other polymer molecules in the reaction. When half of dex-VS was replaced by HA-VS, the gelation time increases because the VS on HA was less reactive to SH.

Example 10: Gelation of Multi-Vinylsulfone Containing Polymer, Multi-Nucleophile Containing Polymer and a Viscosity Modulating Agent after a Time Elapses Vinylsulfonated HA (HA-VS) and HA-SH of MW 108 kDa and 10% DM were dissolved in an HA solution at 2% concentration separately. The HA solution contains 6% 108 kDa HA dissolved in PBS. The HA solution acted as a viscosity modulation agent. After mixing the two polymer solutions and waited for 30 minutes, the mixture were aspirated by the syringe and injected under a skin of a mouse to the subcutaneous space of the mouse. A hydrogel was formed after injection and it was visible for more than half a year until it is gradually degraded by enzymes in the body.

Example 11: Gelation of Multi-Vinylsulfone Containing Polymer, Multi-Nucleophile Containing Polymer and a Physically Crosslinkable Agent after a Time Elapses Dex-VS of MW 70 kDa and 12% DM, dex-SH of MW 70 kDa and 12% DM, were dissolved in PBS at 12% concentration. Because the VS and SH are relatively hydrophobic chemical moieties, higher loading of these groups on the polymer will decrease the solubility of the polymer and make them easier to aggregate. In this example the dex-VS and dex-SH are both chemically crosslinkable polymer and physically crosslinkable polymer. The polymer solutions were mixed and an opaque hydrogel was formed shortly after mixing.

In another example, Dex-VS of MW 40 kDa and 4% DM, dex-SH of MW 40 kDa and 4% DM, are dissolved at 15% (w/v) concentration in a phosphate buffered solution containing 1.5% alginate. The polymers are mixed and the gel is formed. This gel is stronger than the gel without alginate (FIG. 1).

In another example, Dex-VS of MW 40 kDa and 4% DM, dex-SH of MW 40 kDa and 4% DM, are dissolved at 15% (w/v) concentration in a phosphate buffered solution containing 1.5% alginate. After mixing, the gel is formed. The gel with calcium is stronger, can deform more and more resistance to fracture than gel with sodium (FIG. 1).

In another example, Dex-VS of MW 40 kDa and 4% DM, dex-SH of MW 40 kDa and 4% DM, are dissolved at 15% (w/v) concentration in a phosphate buffered solution containing 1.5% alginate and calcium sulphate. The gel with calcium phosphate is stronger, can deform more and more resistance to fracture than gel without calcium phosphate.

To control the gelation time, the pH of PBS was adjusted to 6.5, 7 and 7.4. The fastest gelation happed in pH 7.4. A pH 6.5 caused the gelation to slow down to about 5 minutes.

Another way to control the gelation time is to control the concentration of the polymer. When the polymer concentration was decreased from 12% to 3%, the gelation time extended to about 40 minutes.

Another way to control the gelation time is to control the molecular weight of the polymer. When the MW of dextran was decreased to 40 kDa, the gelation time increased.

Another way to control the gelation time is to include other polymer molecules in the reaction. When half of dex-VS was replaced by HA-VS, the gelation time increased because the VS on HA is less reactive to SH.

Example 12: Gelation of Multi-Vinylsulfone Containing Polymer, Multi-Nucleophile Containing Polymer, a Physically Crosslinkable Agent and an Viscosity Modulation Agent Dex-VS of MW 70 kDa and 12% DM, dex-SH of MW 70 kDa and 12% DM, were dissolved in a hyaluronic acid (HA) solution at 25% concentration. The HA solution contains 1.5% concentration of 1.5 mDa HA in PBS. Because the VS and SH are relatively hydrophobic chemical moieties, higher loading of these groups on the polymer will decrease the solubility of the polymer and make them easier to aggregate. In this example the dex-VS and dex-SH are both chemically crosslinkable polymer and physically crosslinkable polymer. HA is the viscosity modulation agent. The polymer solutions were mixed and an opaque gel was formed shortly after mixing.

Example 13: Encapsulation of Molecules in the Hydrogel and Gelation of Multi-Vinylsulfone Containing Polymer and Multi-Nucleophile Containing Polymer Dex-VS of MW 70 kDa and 8% DM, dex-SH of MW 70 kDa and 8% DM, were dissolved in PBS separately. A radiocontrast agent Omnipaque was added to the precursor solution. The polymer solutions were mixed and a gel was formed. The Omnipaque was slowly released from the hydrogel.

Example 14: Functionalization of Hydrogle and Gelation of Multi-Vinylsulfone Containing Polymer and Multi-Nucleophile Containing Polymer A cell adhesive peptide CG4REDV was first conjugated to the Dex-VS of MW 70 kDa and 8% DM via click chemistry between the VS group and the thiol group of the cysteine of the peptide at physiological pH and temperature. Afterwards, the peptide conjugated polymer were purified and dissolved in PBS at 15% concentration. Dex-SH was dissolved in PBS at 15% concentration. After mixing the two polymers, a hydrogel was formed.

Example 15: Encapsulation of Molecules in the Hydrogel and Triggered Chemical Gelation of Multi-Vinylsulfone Containing Polymer and Multi-Nucleophile Containing Polymer in a Blood Vessel Simulation System Dex-VS of MW 70 kDa and 8% DM, dex-SH of MW 70 kDa and 8% DM, were dissolved in water or normal saline at 25% concentration. The water or normal saline in this area of the world (Hong Kong) has a pH around 5.3 to 5.5. A dye from ink was added to the solution at 1% concentration. The polymer solutions were mixed and loaded to a syringe. A microcatheter of about 0.4 mm inner diameter was attached to the syringe and the solution were injected into a blood vessel simulating tube. The tube has an inner diameter about 1 mm and is continuously flushing with PBS. Shortly after injection, a hydrogel was formed inside the vessel simulating tube.

Figure 2:
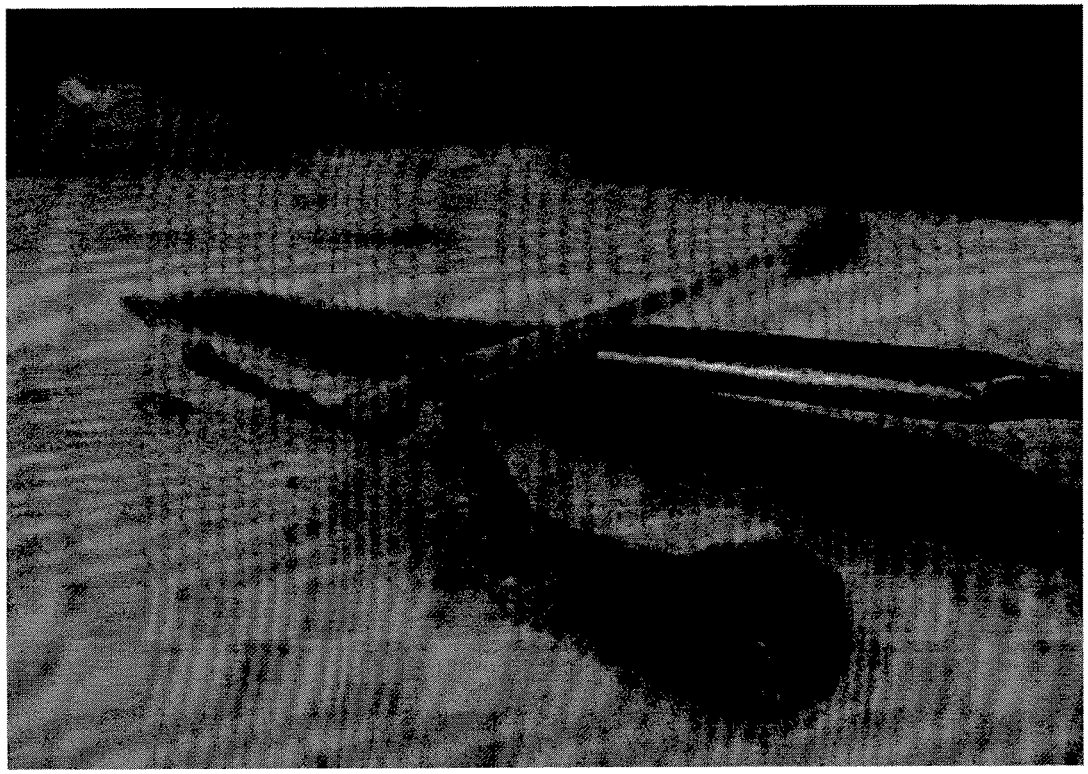
FIG. 2 shows a hydrogel of the present invention extruded out from a vessel-mimicking tube.

Example 16: Encapsulation of Molecules in the Hydrogel and Gelation of Multi-Vinylsulfone Containing Polymer and Multi-Nucleophile Containing Polymer after a Time Elapses in a Blood Vessel Mimicking Tube Dex-VS of MW 70 kDa and 4% DM, dex-SH of MW 70 kDa and 3% DM, were dissolved in pH 7.4 PBS at 15% concentration separately. A dye from ink was added to the solution at 1% concentration. The polymer solutions were mixed and loaded into a syringe. A microcatheter of about 0.4 mm inner diameter was attached to the syringe and the solution was injected into a blood vessel mimicking tube after 2 minutes. The tube had an inner diameter about 1 mm and was filled with PBS. A hydrogel was formed inside the vessel mimicking tube (FIG. 2).

Figure 3:
FIG. 3 shows a hydrogel of the present invention in the coronary artery of a porcine heart after injection.

Example 17: Encapsulation of Molecules in the Hydrogel and Gelation of Multi-Vinylsulfone Containing Polymer and Multi-Nucleophile Containing Polymer after a Time Elapses in Ex Vivo Animal Blood Vessel Model Dex-VS of MW 70 kDa and 4% DM, dex-SH of MW 70 kDa and 3% DM, were dissolved in PBS of pH 7.4 at 15% concentration separately. A dye from ink was added to the solution at 1% concentration. The polymer was mixed for 2 minutes and injected into the coronary artery of a porcine heart that was previously filled with PBS through a catheter. A gel was formed in the blood vessel (FIG. 3).

Figure 4:
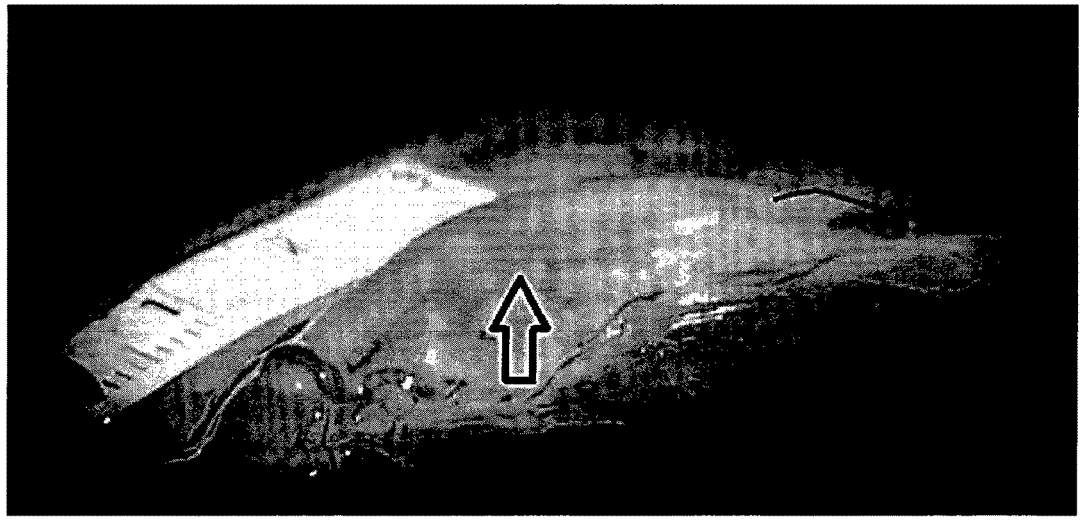
FIG. 4 shows a hydrogel of the present invention in a blood vessel. The arrow indicates the location of the gel and blood vessel.

Example 18: Encapsulation of Molecules in the Hydrogel and Chemical Gelation of Multi-Vinylsulfone Containing Polymer and Multi-Nucleophile Containing Polymer after a Time Elapses in Ex Vivo Human Placenta Model Dex-VS of MW 70 kDa and 4% DM, dex-SH of MW 70 kDa and 4% DM, were dissolved in PBS of pH 7.4 at 15% concentration separately. A dye from ink was added to the solution at 1% concentration. The polymer solutions were mixed and loaded into a syringe. After a time elapse the solution was injected into the blood vessel of human placenta through a catheter with continuous perfusion of PBS using another catheter on the same vessel. The hydrogel was formed after injection (FIG. 4).

Figures 5A, 5B:
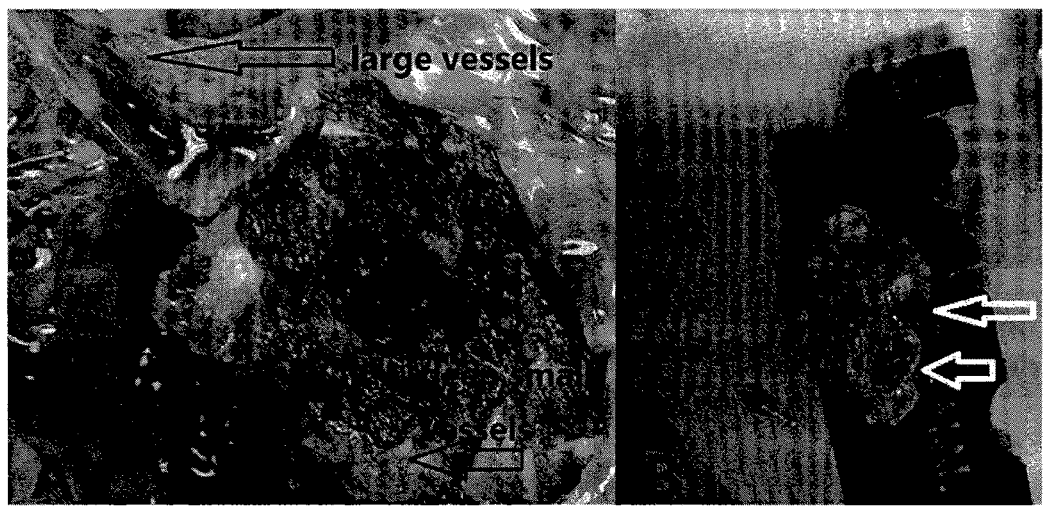
FIG. 5 shows (A) hydrogel of the present invention in the deep and small vessels and (B) hydrogel clearly seen in blood vessels (arrow) after dissection.

Example 19: Encapsulation of Molecules in the Hydrogel and Triggered Chemical Gelation of Multi-Vinylsulfone Containing Polymer and Multi-Nucleophile Containing Polymer in Ex Vivo Human Placenta Model Dex-VS of MW 70 kDa and 10% DM, dex-SH of MW 70 kDa and 10% DM were dissolved in a normal saline at the concentration of 28% separately. A dye from ink was also added to the solution at 1% concentration. The polymer solutions were mixed and loaded into a syringe. The solution mixture was injected into the blood vessel of human placenta through a catheter with continuous perfusion of PBS using another catheter on the same vessel. A hydrogel was formed inside the blood vessel. The polymer can flow into deep and small blood vessel and form gel (FIG. 5).

Figures 6A, 6B:
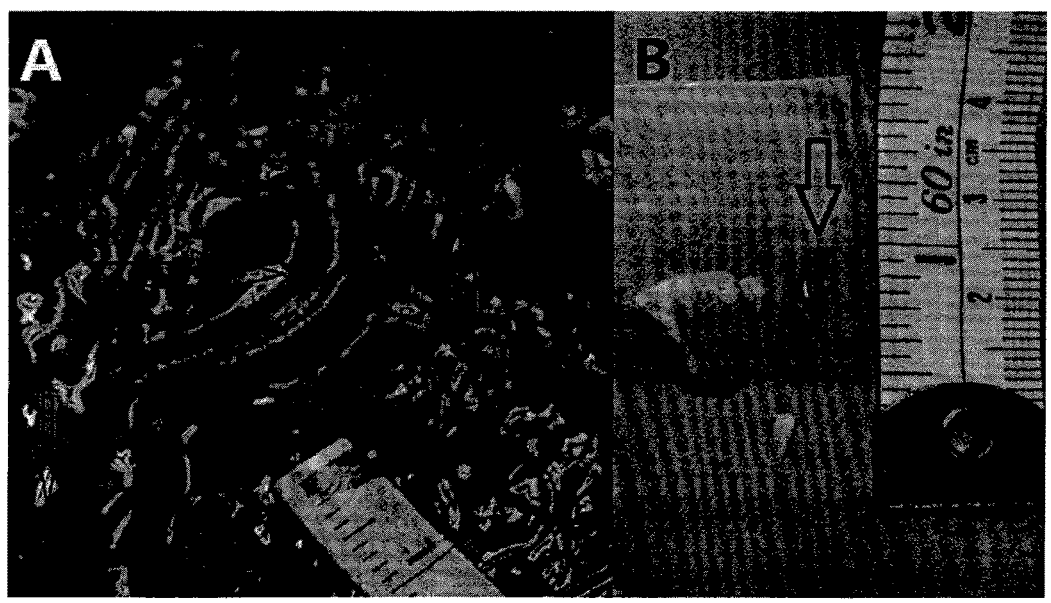
FIG. 6 shows (A) hydrogel of the present invention in a large blood vessel. Arrows indicate the location of gel and blood vessel. (B) shows a hydrogel segment (arrow) extruded from a blood vessel after dissection.

Example 20: Encapsulation of Molecules in the Hydrogel and Triggered Chemical Gelation of Multi-Vinylsulfone Containing Polymer and Multi-Nucleophile Containing Polymer and a Viscosity Modulation Agent in Ex Vivo Human Placenta Model Dex-VS of MW 70 kDa and 6% DM, dex-SH of MW 70 kDa and 6% DM were dissolved in a normal saline containing 1.5% 1.5 mDa hyaluronic acid at the concentration of 23% separately. A dye from ink was also added to the solution at 1% concentration. The polymer solutions were mixed and loaded into a syringe. The solution mixture was injected into the blood vessel of human placenta through a catheter with continuous perfusion of PBS using another catheter on the same vessel. A hydrogel was formed inside the blood vessel and the gel was able to occlude large vessels (FIG. 6).

Example 21: Biocompatibility of Hydrogel

Figure 7:
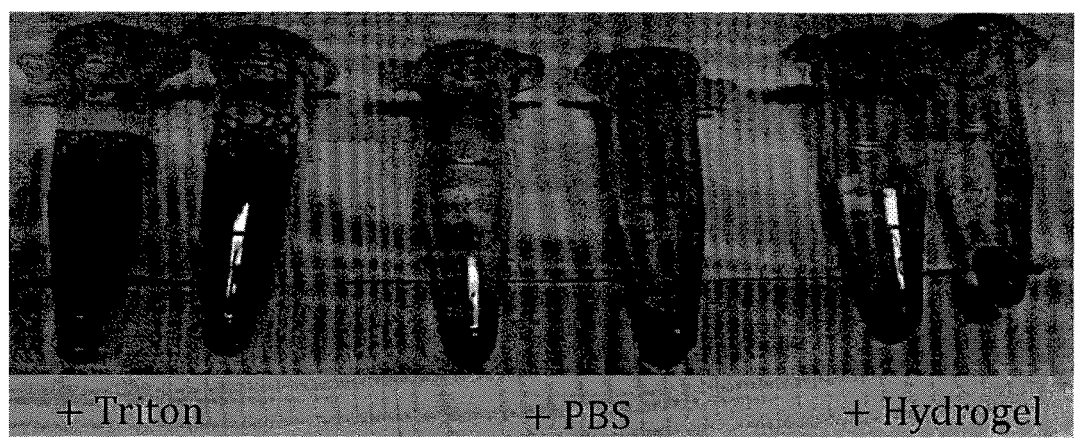
FIG. 7 shows a hemolytic assay for hydrogel of the present invention.

The hydrogel was tested for hemolysis. Heparinized fresh rabbit blood was centrifuged at 2000 rpm for 10 min. The supernatant was removed. The red blood cells were then resuspended in warm PBS. Resuspend the cells pellet in warm PBS of proper volume to prepare 8% (v/v) erythrocyte PBS suspension and aliquot 0.5 mL in tubes. Hydrogel composed of Dex-VS of MW 70 kDa and 5% DM, dex-SH of MW 70 kDa and 5% DM at concentration of 20% were added to obtain a final erythrocyte concentration of 4% (v/v). PBS and 1% Triton X-100 were used as negative and positive control respectively. The resulting suspensions were incubated at 37° C. for 1 h at agitation of 300 rpm, followed by centrifugation at 2000 rpm for 10 min. The absorbance of supernatant at 540 nm was measured to examine the release of hemoglobin to reflect the damage of erythrocyte membrane. The percentage of hemolysis of the gel was calculated at a negligible 0.0168%. The result shows that the hydrogel will not cause hemolysis (FIG. 7).

Example 22: Effect of Hydrogel on Viability of Endothelial Cells

Figure 8:
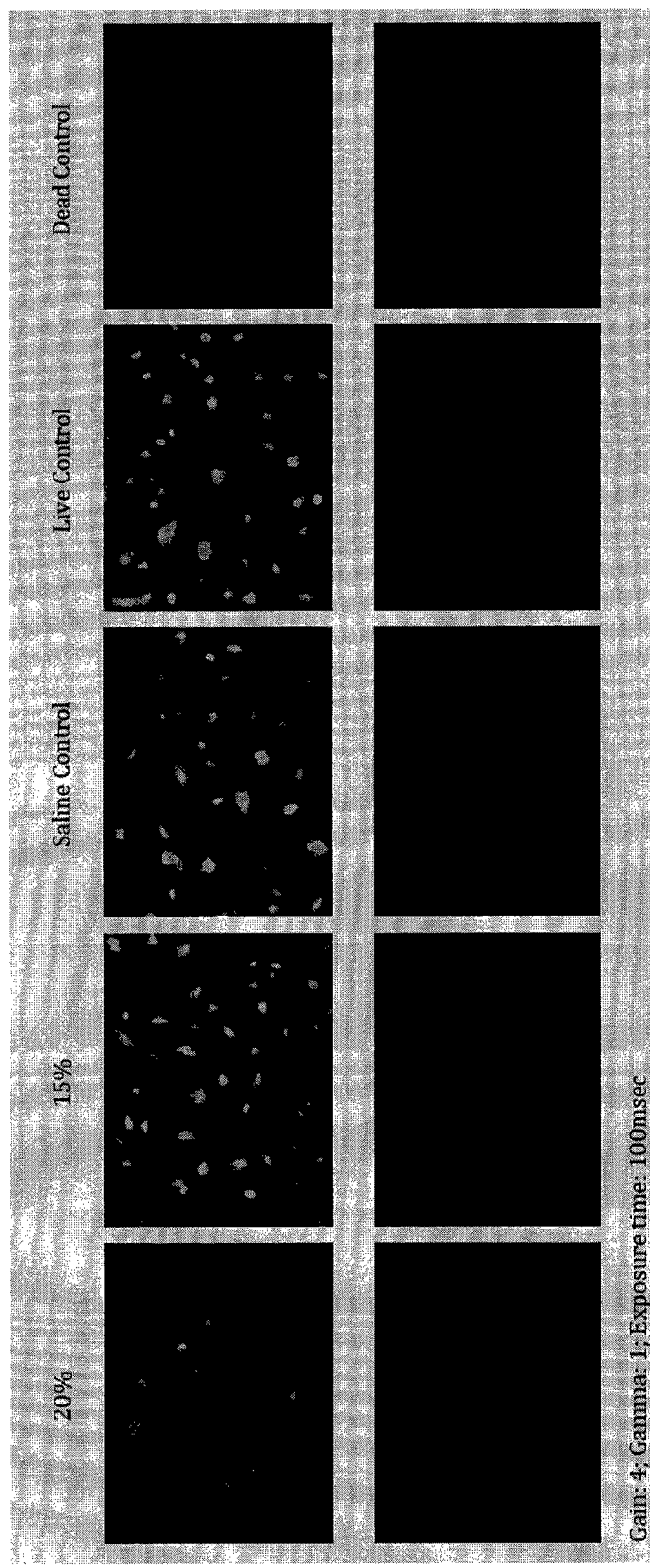
FIG. 8 shows a Live/Dead assay for a hydrogel of the present invention.

A Live/Dead assay was used to examine the effect of hydrogel on viability of endothelial cells. Human umbilical vein endothelial cell (HUVEC) was seeded in 24-well plate with buffered culture medium of pH 7.4. Dex-VS and Dex-SH were dissolved in normal saline (non-buffered, pH 5.3) respectively then mixed at equal volume and added to the cell. Same volume of normal saline without polymer was used as control. After 24 h incubation, cells were stained with calcein AM and EthD-1 from Live/Dead® Viability/Cytotoxicity Kit and examined with a Nikon CFI60 infinity optical system. The result shows that the gelation and incubation with gel caused negligible cell death (FIG. 8)

It is to be appreciated that the foregoing Detailed Description section, and not the Abstract section, is intended to be used to interpret the claims. The Abstract section may set forth one or more, but not all, exemplary embodiments of the present invention as contemplated by the inventor(s), and thus, is not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

Numerical data, such as temperatures, concentrations, times, ratios, and the like, are presented herein in a range format. The range format is used merely for convenience and brevity. The range format is meant to be interpreted flexibly to include not only the numerical values explicitly recited as the limits of the range, but also to include all the individual numerical values or sub-ranges encompassed within the range as if each numerical value and sub-range is explicitly recited. When reported herein, any numerical values are meant to implicitly include the term "about." Values resulting from experimental error that can occur when taking measurements are meant to be included in the numerical values.

What is claimed is:

1. A composition comprising:
   an aqueous solution of at least two chemically crosslinkable polymers, wherein the aqueous solution including the at least two chemically crosslinkable polymers is at a non-physiological physical-chemical condition comprising at least one of: a temperature below 10° C., and a pH of 6.5 or lower;
   wherein the at least two chemically crosslinkable polymers comprise a first polymer and a second polymer,
   wherein the first polymer comprises at least one molecule selected from acrylate, maleimide, vinylsulfone, N-hydroxysuccinimide, aldehyde, and iodoacetyl,
   wherein the second polymer comprises at least one molecule selected from mercaptonicotinamide, quinone, thiol, and amine,
   wherein the aqueous solution is non-buffered saline in which the at least two chemically crosslinkable polymers are dissolved, and
   wherein the aqueous solution is not a hydrogel and is in a non-gelling state.

2. The composition of claim 1, further comprising a viscosity modulating agent.

3. The composition of claim 1, further comprising at least one of a physically crosslinkable agent and a viscosity modulating agent.

4. The composition of claim 1, wherein each chemically crosslinkable agent is a polysaccharide.

5. The composition of claim 2, wherein the viscosity modulating agent is a salt or a polymer that changes the viscosity of the aqueous solution.

6. The composition of claim 2, wherein the viscosity of the aqueous solution after modulation is 0.5 Centipoise to 100000 Centipoise.

7. The composition of claim 1, further comprising at least one of a salt, an organic solvent, a drug, and an imaging agent.

8. The composition of claim 1, further comprising at least one of a drug and an imaging agent that is conjugated on at least one of the chemically crosslinkable agent, a physically crosslinkable agent, and a viscosity modulating agent.

9. The composition of claim 1, wherein the chemically crosslinkable agent comprises at least one polymer selected from hyaluronic acid, polyethylene glycol, dextran, carboxymethyl cellulose, polyvinyl alcohol, alginate, and cyclodextran.

10. A method of forming a hydrogel within a space in a body, comprising:
    injecting a composition according to claim 1 into the space;
    triggering the formation of a hydrogel within the space, the triggering occurring when the aqueous solution contacts at least one of the body and a body fluid within the space; and
    allowing the hydrogel to form within the space.

11. The method of claim 10, wherein the forming of the hydrogel comprises covalently bonding the at least two chemically crosslinkable polymers.

12. The method of claim 10, wherein the aqueous solution further comprises at least one of a physically crosslinkable agent and a viscosity modulating agent.

13. The method of claim 12, wherein the forming of the hydrogel comprises physically bonding the physically crosslinkable agent.

14. The method of claim 10, wherein the triggering of the formation of a hydrogel further comprises a trigger by a change in at least one of temperature, ionic strength, salt composition, organic solvent content, and water content, when the solution is in contact with at least one of the body and the body fluid.

15. The method of claim 14, wherein the change in temperature trigger comprises a temperature difference between the solution being injected, at a temperature below 10 degrees Celsius, and a body fluid, at a temperature between 25 and 45 degrees Celsius.

16. The method of claim 10, wherein the forming of the hydrogel takes 1 second to 2 hours.

17. The method of claim 10, wherein the space in the body is a lumen in the body.

18. The method of claim 10, wherein the space in the body is a cavity in the body.

19. The method of claim 10, wherein the composition further comprises a drug.

20. The composition of claim 1, wherein the first polymer comprises a vinylsulfone, and wherein the second polymer comprises a thiol.

21. The composition of claim 1, wherein the composition is configured such that, when in contact with a body or body fluid at a physiological physical-chemical condition comprising a buffered system at a pH in a range of from 7.0 to 8.0 and a temperature in a range of from 30° C. to 40° C., the aqueous solution is triggered by exposure to the physiological physical-chemical condition into forming a hydrogel by a chemical crosslinking reaction between the chemically crosslinkable polymers.

22. The composition of claim 1, wherein the non-buffered saline is normal saline.

23. A composition for drug delivery comprising a composition according to claim 1 that further comprises a drug.

* * * * *